US008262622B2

(12) United States Patent
Gonzales et al.

(10) Patent No.: US 8,262,622 B2
(45) Date of Patent: Sep. 11, 2012

(54) SURGICAL GEL SEAL

(75) Inventors: Joseph A. Gonzales, Tehachapi, CA (US); Boun Pravong, Corona, CA (US); Richard C. Ewers, Fullerton, CA (US); Richard L. Myers, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1435 days.

(21) Appl. No.: 10/695,295

(22) Filed: Oct. 28, 2003

(65) Prior Publication Data
US 2005/0090713 A1  Apr. 28, 2005

(51) Int. Cl.
*A61M 5/178* (2006.01)
*A61B 1/307* (2006.01)

(52) U.S. Cl. ............... 604/167.01; 600/135; 600/159

(58) Field of Classification Search ............ 604/167.01–167.06, 256; 600/135, 600/159
See application file for complete search history.

(56) References Cited

U.S. PATENT DOCUMENTS

| | | | | |
|---|---|---|---|---|
| 4,143,853 A * | 3/1979 | Abramson | ............ | 251/149.1 |
| 4,475,548 A | 10/1984 | Muto | | |
| 4,946,133 A * | 8/1990 | Johnson et al. | ............ | 251/149.1 |
| 5,104,389 A | 4/1992 | Deem et al. | | |
| 5,195,980 A | 3/1993 | Catlin | | |
| 5,226,891 A | 7/1993 | Bushatz et al. | | |
| 5,360,417 A * | 11/1994 | Gravener et al. | ............ | 604/278 |
| 5,385,553 A | 1/1995 | Hart et al. | | |
| 5,456,284 A | 10/1995 | Ryan et al. | | |
| 5,460,616 A * | 10/1995 | Weinstein et al. | ....... | 604/167.03 |
| 5,476,475 A | 12/1995 | Gadberry | | |
| 5,514,109 A * | 5/1996 | Mollenauer et al. | .......... | 604/249 |
| 5,709,664 A | 1/1998 | Vandenbroek et al. | | |
| 5,782,812 A | 7/1998 | Hart et al. | | |
| 5,803,919 A | 9/1998 | Hart et al. | | |
| 5,911,710 A | 6/1999 | Barry et al. | | |
| 5,971,960 A | 10/1999 | Flom et al. | | |
| 6,159,182 A | 12/2000 | Davis et al. | | |
| 6,287,280 B1 | 9/2001 | Iampropoulos et al. | | |
| 6,575,960 B2 | 6/2003 | Becker et al. | | |
| 2003/0139756 A1* | 7/2003 | Brustad | ....................... | 606/167 |
| 2003/0194277 A1* | 10/2003 | Courtney | ....................... | 405/186 |
| 2003/0222384 A1* | 12/2003 | Kato et al. | ................. | 267/141.2 |
| 2004/0015186 A1 | 1/2004 | Ewers et al. | | |

OTHER PUBLICATIONS

International Searching Authority, International Search Report and Written Opinion for International Application PCT/US04/29853, mailed Feb. 24, 2006.

* cited by examiner

*Primary Examiner* — Quynh-Nhu H Vu
(74) *Attorney, Agent, or Firm* — Patrick Y. Ikehara; Pui Tong Ho; David G. Majdali

(57) ABSTRACT

A surgical valve includes a housing with a proximal housing portion and a distal housing portion cooperating to define a gel cavity. A seal material is disposed in the gel cavity and includes a gel having flow characteristics and incompressible characteristics. A distal guide tube is provided to facilitate retrograde insertion of a surgical instrument into the seal material. During assembly, pressure is applied by the housing portions to the seal material in order to form a circumferential seal and to close an instrument channel. Manufacture can be facilitated by use of a mandrel for maintaining the structural elements in axial alignment. Complimentary screw threads disposed between the first and second housing portions can be used to pressurize the gel and thereby create a locking force on an inserted instrument. Detented tabs can be provided to facilitate control of this locking force.

14 Claims, 7 Drawing Sheets

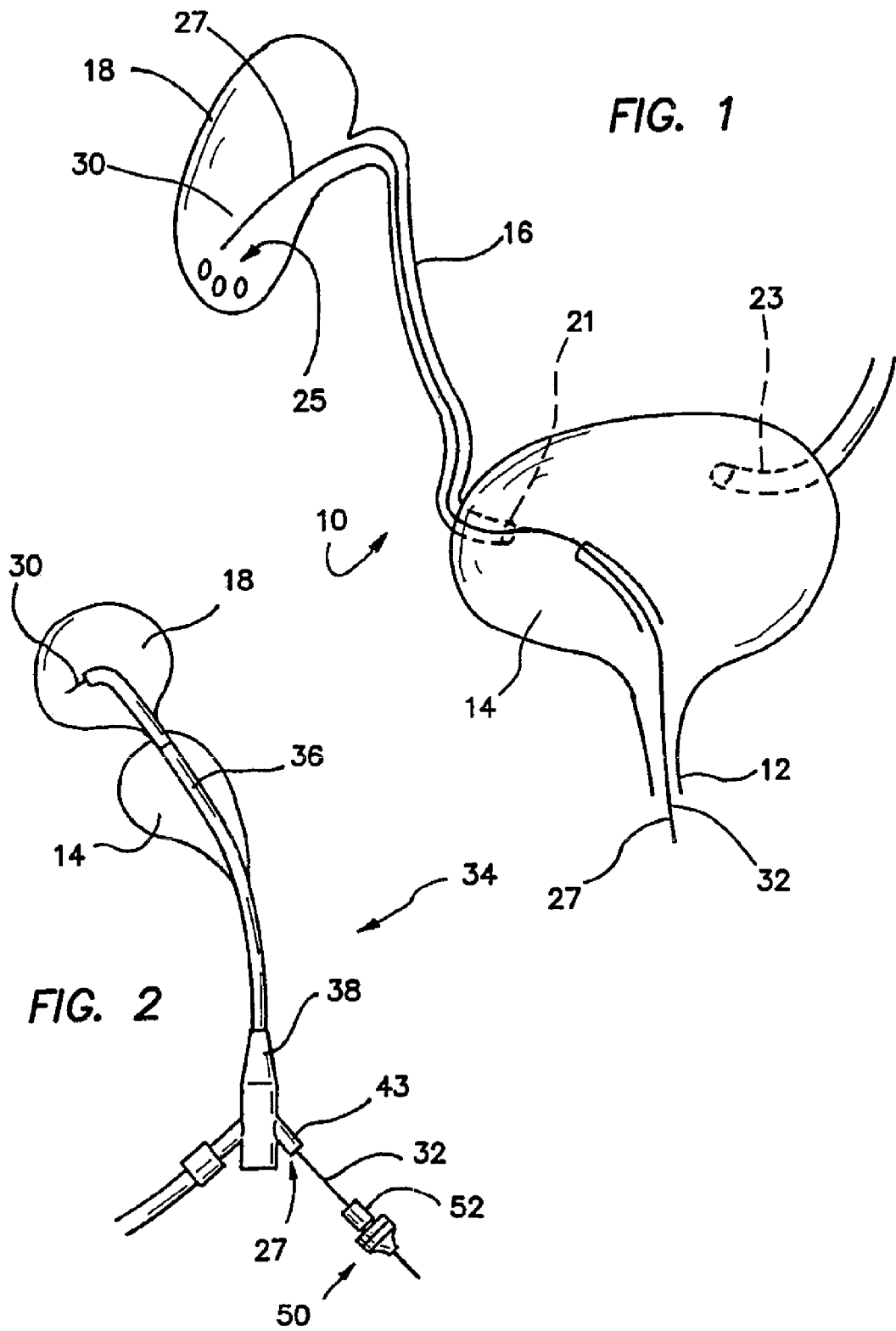

SURGICAL GEL SEAL

BACKGROUND OF THE INVENTION

1. Field of the Invention

This invention relates generally to medical and surgical devices and more specifically to access seals adapted for use in urological procedures.

2. Discussion of the Relevant Art

There are many procedures which involve the exploration, visualization and manipulation of body conduits such as the vascular system, digestive tract, and urinary tract. Notwithstanding the wide application of the present invention, a more detailed description will be undertaken only with respect to a single field of use.

In the urinary tract it is well known that stones, which commonly form in the kidneys and the bladder, often need to be surgically removed. This procedure is typically undertaken using a ureteroscope having a working channel that is accessible through an exit port. Initially, a guidewire is threaded through the urinary tract, perhaps with the assistance of a cystoscope. Once the guidewire is in place, the ureteroscope can be advanced over the guidewire which is back-loaded into the working channel of the ureteroscope. Once the ureteroscope is in place, it is used to visualize the interior of the kidney, for example.

This visualization is enhanced by irrigating the kidney through the ureterscope. This irrigation fluid which is typically introduced to a separate channel in the ureteroscope nevertheless tends to fill the working channel. Within the working channel, the irrigation fluid would flow retrograde through the exit port contaminating the surgical site were it not for a urology seal placed over the exit port. In the past, these urology valves have typically been provided with an elastomeric septum or duckbill having characteristics for forming both a zero seal in the absence of an instrument, such as the guidewire and to form an instrument seal in the presence of the instrument. Both of these valves rely upon force more than compliance for their sealing characteristics. Accordingly, there is significant resistance associated with the introduction and removal of instruments through these urology valves. These valves also accommodate a very limited range of instrument sizes and tend to degrade over a short period of time.

SUMMARY OF THE INVENTION

In accordance with the present invention, an access valve is provided for use in establishing a zero seal or instrument seal across any body conduit. In the urology procedure previously discussed, the valve is of primary interest.

It is of particular advantage that the access valve of the present invention is provided with a gel material which provides the sealing characteristics for the valve. Within the valve, the gel functions with properties that are partly liquid and partly solid. The gel has solid properties to the extent that it can be provided with an initial form, and cohesion properties sufficient to maintain the gel in a single contiguous piece. The gel has liquid properties to the extent that it can be pushed to flow in the direction of least resistance and is generally non-compressible. These and other features of the gel are disclosed in applicant's co-pending PCT application, serial number PCT/US01/29682 filed on Sep. 21, 2001 and entitled Surgical Access Apparatus and Method which is incorporated herein in its entirety by reference.

In order to accommodate the gel within the valve and otherwise provide additional features and advantages for the valve, other structural modifications can be made. For example, the housing for the valve can be formed with both a distal portion and a proximal portion which define a gel cavity. (It should be noted that throughout this is specification, the words "proximal" and "distal" are measured relative to the surgeon not the patient.) Lead-in tubes can be provided in both portions to facilitate both forward and retrograde loading of the valve. The lead-in tube on the proximal portion of the housing can extend through the housing wall into the gel cavity to contact and compress the gel material during assembly. This will facilitate formation of a circumferential seal between the gel and the housing and will also tend to close an instrument channel through the gel to facilitate formation of a zero seal. Both zero seals and instrument seals can be formed while leaving expansion space within the gel cavity to accommodate displacement of the gel by an instrument.

Alternatively, expansion space can be controlled within the gel cavity in order to pressurize the incompressible gel material and thereby produce a variably locking force on an instrument. Finger tabs can be provided on the distal and proximal portions to facilitate control of the variable pressure through various de-tented positions of the tabs.

In one aspect, the invention includes a surgical valve having an axis that extends between a proximal end and a distal end. The valve includes a housing having a proximal housing portion and a distal housing portion which cooperate to define a gel cavity. A seal material is disposed in the gel cavity and includes a gel having non-compressible characteristics. A proximal guide tube which extends axially proximally from the proximal housing portion, facilitates insertion of a surgical instrument into the seal material. A distal guide tube which extends axially distally from the distal housing portion, facilitates retrograde insertion of the surgical instrument into the seal material. The proximal guide tube includes interior portions which extend distally of the proximal housing portions to contact the gel around an axial channel extending through the gel.

In another aspect, a surgical valve includes a first housing portion defining a gel cavity, and a seal material including a gel and having a node and an axial channel. A subassembly includes the seal material disposed in the gel cavity, the seal material being formed with a channel in an open state. A second housing portion, disposed in juxtaposition to the first housing portion, applies a force to the seal material in the subassembly, the force being of a magnitude sufficient to place the channel in a closed state. This force has a magnitude which is also sufficient to create a circumferential seal between the seal material in the first housing portion. The force is created by contact between an axial guide tube of the second housing portion which extends into the gel cavity contacting the node and applying the force to the seal material.

In a further aspect of the invention, a surgical valve is adapted to form a seal around a surgical instrument extending through the valve. First and second housing portions define a gel cavity having a volume and being adapted to receive a gel having properties including flowability and incompressibility. The gel also has characteristics for creating a pressure on the instrument to form a seal with the instrument. Means is provided to move the second housing portion relative to the first housing portion to increase the pressure of the incompressible gel on the instrument and to create a locking force tending to inhibit movement of the instrument relative to the valve. The moving means can include complimentary screw threads, disposed on the first and second housing portions, which facilitate axial movement to reduce the volume of the gel cavity and increase the pressure of the incompressible gel on the instrument.

In another aspect, the invention includes a method for manufacturing a surgical valve including the step of providing a seal material in the form of a gel having non-compressible characteristics. A housing is provided, including a first housing portion and a second housing portion which define a gel cavity. The seal material is mounted in the first housing portion in a loose-fit relationship, and the second housing portion is moved into a proximal relationship with the first housing portion. During this moving step a force is applied to the gel which causes the gel to flow into a sealing relationship with at least the first housing portion. This force is applied through a guide tube of the second housing portion which extends into the gel cavity. During the mounting step, the first and second housing portions, as well as the seal material, can be mounted on a mandrel in order to facilitate axial alignment during the moving step.

In still a further aspect, the invention includes a method for accessing a kidney of a patient in a urological procedure. A guidewire is placed in the patient, the guidewire having a proximal end, and a distal end extending through a urethra, a bladder, and into the kidney of the patient. The proximal end of the guidewire is inserted retrograde into a channel of an endoscope. The endoscope is then moved over the guidewire to access the kidney, leaving the proximal end of the guidewire extending from the channel of the endoscope. A urological valve is provided, having a proximal end and a distal end, and a seal material in the form of an incompressible gel disposed therebetween. The valve is loaded retrograde onto the proximal end of the guidewire to form a seal between the incompressible gel and the guidewire. Mounting the distal end of the valve to the endoscope seals the channel of the endoscope around the guidewire.

These and other features and advantages of the invention will become more apparent with a discussion of preferred embodiments and reference to the associated drawings.

DESCRIPTION OF THE DRAWINGS

FIG. 1 is a schematic view of the left side of a urinary tract showing a guidewire extending from the urethra into a kidney;

FIG. 2 is a schematic view of the urinary tract showing a ureteroscope threaded over the guidewire and a surgical valve of the present invention positioned to extend over the guidewire to close an exit port of a working channel;

DESCRIPTION OF PREFERRED EMBODIMENT AND BEST MODE OF THE INVENTION

Figure 3:
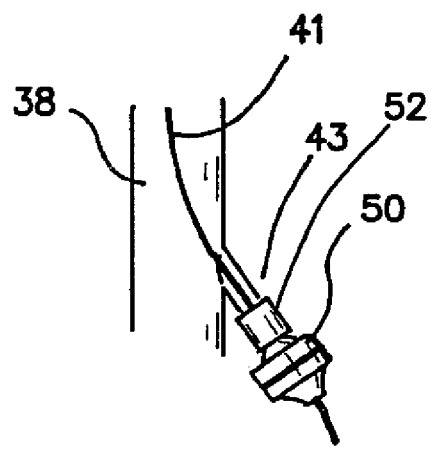
FIG. 3 is a schematic view showing the handle of the ureteroscope with the guidewire removed and the surgical valve ready to receive various instruments.

A urinary tract is illustrated in FIG. 1 and designated by the reference numeral 10. Only the right side of the urinary tract 10 is illustrated showing the urethera 12, bladder 14, right ureter 16 and right kidney 18. The junction of the ureter 16 and bladder 14 is commonly referred to as a urethral orifice 21. A similar orifice 23 is illustrated for the left urinary tract but will not be further discussed in order to simplify the disclosure.

As with most body conduits, many procedures can be undertaken with to respect to the urinary tract 10, most of which require some degree of exploration, visualization and manipulation of the tract 10

By way of example, a plurality of stones 25 is illustrated in the kidney 18 to facilitate discussion of a common stone removal procedure. As illustrated in FIGS. 1-3, a guidewire 27, having a floppy distal end 30 and a proximal end 32, is initially passed through the urinary tract 10 beginning at the urethera 12 and ending at the kidney 18. In order to facilitate placement of the floppy guidewire 27, a cystoscope (not shown) may be used primarily to facilitate introduction of the guidewire 27 into the urethral orifice 21.

Once the guidewire is in place, a ureterscope 34 can be introduced into the urinary tract 10. The ureterscope 34 has an elongate shaft 36 extending from a handle 38, and typically includes fiberoptics (not shown) to facilitate visualization, and a working channel 41 which terminates proximally at an exit port 43 on the handle 38.

With the ureterscope 34 thus positioned over the guidewire 32, visualization of the interior regions of the kidney 18 can be undertaken. This visualization is greatly facilitated by irrigating and aspirating the kidney 18 with saline which is typically introduced through a separate channel in the ureteroscope 34. During this procedure, the irrigation fluid will have a tendency to flow retrograde through the working channel and out the exit port where it can severely contaminate the surgical site. In order to prevent this contamination, a urology valve 50 of the present invention can be placed over the exit port to provide a zero seal in the absence of an instrument and an instrument seal in the presence of an instrument, such as the guidewire 27.

With the proximal end 32 of the guidewire 27 extending from the exit port 43, the urology valve 50 can nevertheless be positioned by introducing the guidewire 27 retrograde into the valve 50, and attaching the valve 50 to the exit port 43 by means of a Luer fitting 52

This retrograde insertion of the guidewire 27 into the valve 50 has presented a particular problem in the past where elastomeric sealing materials have been used to form a duckbill or septum valve. These valves are commonly configured to facilitate introduction of instruments in a forward direction and do not easily accommodate retrograde insertion.

Once the urology valve 50 is in place over the exit port 43 as illustrated in FIG. 3, the guidewire 27 can be removed to vacate the working channel 41. A zero seal is immediately formed by the valve 50 in the absence of an instrument.

Figure 4:
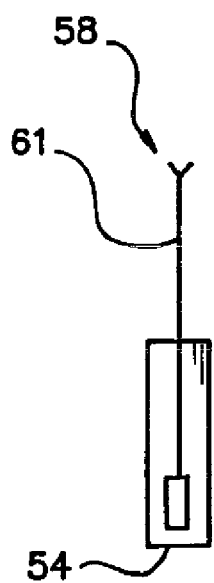
FIG. 4 is a grasper instrument for use with the surgical gel seal of the present invention.
Figure 5:
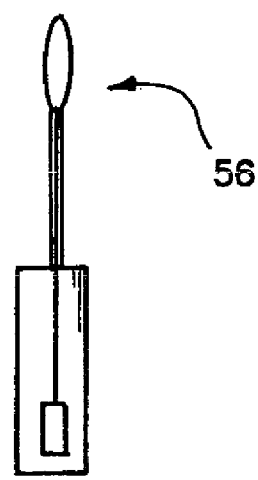
FIG. 5 stone basket instrument for use with the surgical gel seal of the present invention.

The introduction of various instruments to facilitate the engagement capture and withdrawal of the stones 25 (FIG. 1) can now be introduced through the urology valve 50, through the exit port 43, and into the working channel 41. By way of example, a grasper 54 and a stone basket 56 are illustrated in FIGS. 4 and 5, respectively. These instruments will commonly have an operative device, such as grasper arms 58 at the distal end of an elongate flexible shaft 61. In an operative state, the operative device will have a high profile, but in an insertion state the operative device is retracted into the shaft 61 to provide a low-profile state. In the low-profile state, the shaft 61 of such devices will typically have a diameter less than 0.070 inches, a common size for the through-channel of the valve 50.

In order to fulfill all of the functions desired for the urology valve 50, it must accommodate retrograde insertion of a guidewire as well as forward insertion of the instruments, such as the grasper 54. A zero seal must be maintained across the exit port 43 in the absence of an instrument while an instrument seal must be maintained across the exit port 43 in the presence of an instrument. These functions are accomplished in preferred embodiments of the invention which are illustrated, for example, in the exploded views of FIGS. 16 and 6. In both of these embodiments, a seal material 70 in the form of a gel 72 is provided to facilitate formation of both a zero seal and an instrument seal. The gel 72 has excellent elongation and cohesive properties which facilitate both the manifestation and operation of the valve 50. It also has fluid properties which easily accommodate insertion of instruments in both a forward and retrograde direction.

Figure 16:
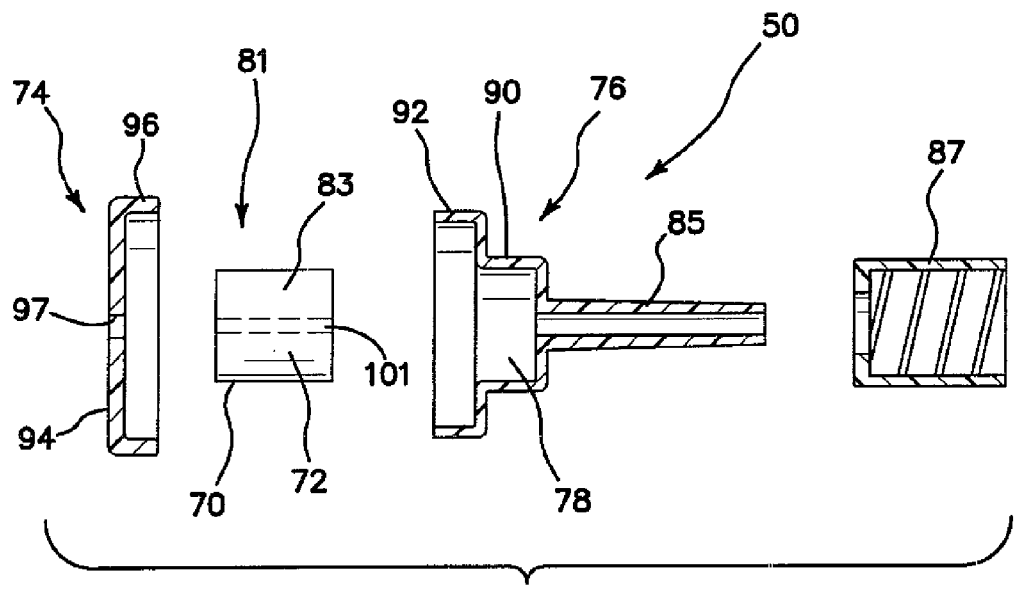
FIG. 16 is a side elevation cross sectional exploded view of one embodiment of the present invention.

The embodiment of FIG. 16 includes a proximal housing portion 74 and a distal housing portion 76 which in this case functions as a cap. A preferred embodiment of the urology valve 50 is illustrated in the cross sectional exploded view of FIG. 16. This embodiment includes a distal housing portion 76, and a proximal housing portion 74 that combine to define a gel cavity 78. This cavity is sized and configured to receive a plug 81 of seal material which in this case advantageously includes the gel 72. A male Luer fitting 85 and associated screw cap 87 extend distally of the distal housing portion 76

The walls of the distal housing portion 76 include a pair of cylindrical walls 90 and 92 with respective diameters which increase in the proximal direction. The proximal housing portion 74 in this embodiment includes a planar wall which extends radially, and together with a cylindrical wall 96, forms a cap for the distal housing portion 76. A hole 97 is formed centrally in the wall 94

The plug 81 including the gel 72 will typically be formed with a cylindrical configuration and an axial channel 101 which is open in an uncompressed state. The diameter of the plug 81 is preferably only slightly more than the inside diameter of the wall 90 to facilitate loading the plug into the gel cavity 78 of the distal housing portion 76.

Figure 17:
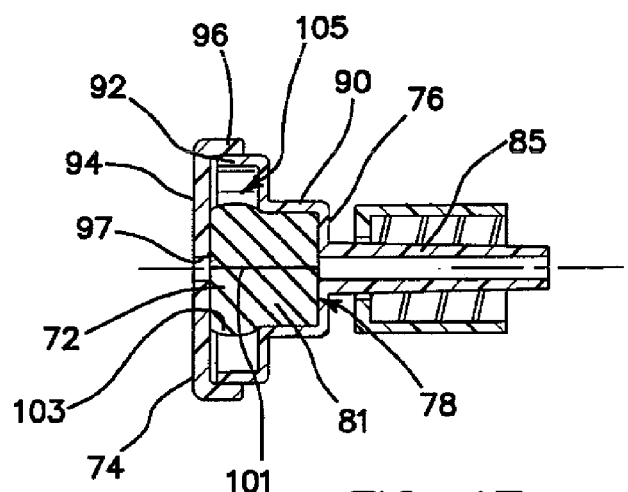
FIG. 17 is a cross sectional assembled view of the embodiment illustrated in FIG. 16.

In its assembled state, illustrated in the cross sectional view of FIG. 17, the plug 81 is disposed in the cavity 78 and the proximal housing portion 74 is brought into a capping relationship with the cylindrical wall 92 of the distal housing portion 76. In this assembled state, the plug 81 is compressed within the seal cavity 78 in order to form a circumferential seal with the cylindrical wall 90 of the distal housing portion 76, and a face seal with the wall 94 of the proximal housing portion 74. Since the plug 81 is composed of the gel 72, it is non-compressible so the applied force is distributed throughout the gel to produce the seals. The pressure within the gel 72 will also tend to create an annular bulge 103, which extends into an expansion portion 105 of the cavity 78 defined by the cylindrical wall 92. This portion 105 of the cavity remains to provide free space into which the gel 72 can further expand as an instrument is inserted through the hole 97 and the channel 101. The pressure within the gel 72 also is sufficient to close the channel 101 so that the plug 81 can function as a zero seal in the absence of an instrument.

Figure 6:
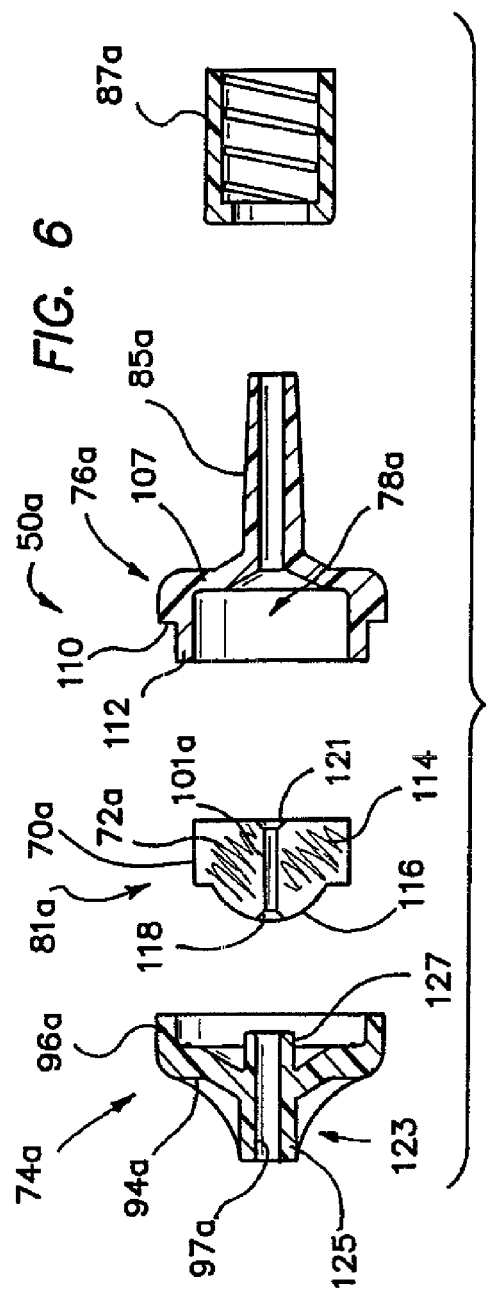
FIG. 6 is a side elevation cross sectional exploded view of an embodiment of the invention.

In a further embodiment of the invention, illustrated in FIG. 6, structure elements similar to those previously described will be provided with the same reference numeral followed by the lower case letter "a" For example, in this embodiment the valve 50a is illustrated in a cross sectional exploded view to include a proximal housing portion 74a, a plug 81a of gel 72a, and a distal housing portion 76a with a luer fitting 85a and an associated screw cap 87a. In this case, the gel cavity 78a is defined progressively proximally by a radially wall 107 having a shoulder 110, and a coaxial cylindrical wall 112

The plug 81a is similar to the plug 81 in FIG. 16 in that it includes a cylindrical portion 114 and the axial channel 101a. In this case, however, a spherical node 116 is formed integral with and proximal of the cylindrical portion 114. The channel 101a also extends through the node 116 and is provided with a lead-in funnel 118 on the proximal end of the plug 81a and a lead-in funnel 121 on the distal end of the plug 81a.

The proximal housing portion 74a is similar to the housing portion 74 of FIG. 16 in that it includes a wall 94a that extends radially outwardly to a coaxial cylindrical wall 96a. In this case however, the proximal housing portion 74a includes a lead-in tube 123 which defines the hole 97a and extends through the wall 94a with a proximal portion 125 and a distal portion 127.

In order to facilitate assembly of the valve 50, the diameter of the cylindrical portion 114 of the plug 81a is preferably provided with a diameter only slightly more than that of the wall 112 which defines the seal cavity 78a. With this lesser dimension, the plug 81a is easily inserted axially into the seal cavity 78a of the distal housing portion 76a. At this point, the plug 81a is only slightly compressed so the channel 101a remains in an open state.

As the proximal housing portion 74a is moved axially to cap the distal housing portion 76a, the cylindrical wall 96a initially engages the cylindrical wall 112 and may ultimately abuts the shoulder 110 of the distal housing portion 76a. As this axial movement progresses, the distal portion 127 of the lead-in tube 123 contacts the node 116 around the funnel 118 of the plug 81a. Further axial movement of the proximal housing portion 74a applies a force to the node 116 which is converted into a pressure throughout the incompressible gel 72a. This pressure forces the channel 101a to a closed state and also moves the cylindrical portion 114 into a sealing relationship with the walls 107 and 112 of the distal housing portion 76a.

Figure 7:
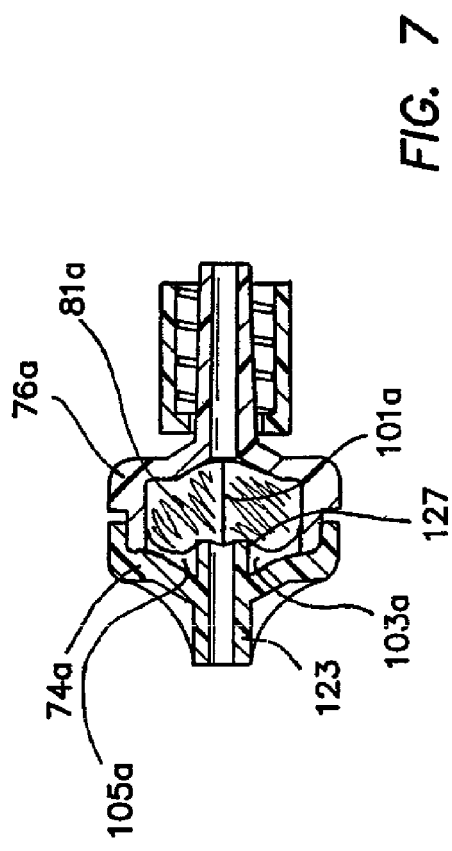
FIG. 7 is a cross sectional assembled view of the valve embodiment illustrated in FIG. 6.

In the assembled state illustrated in FIG. 7, it can be seen that compression of the plug 81a by the distal portion 127 of the lead-in tube 123 also forms an annular bulge 103a which extends slightly into the open cavity portion 105a. This cavity portion 105a accommodates further expansion of the plug 81a when an instrument is inserted through the channel 101a.

Figure 8:
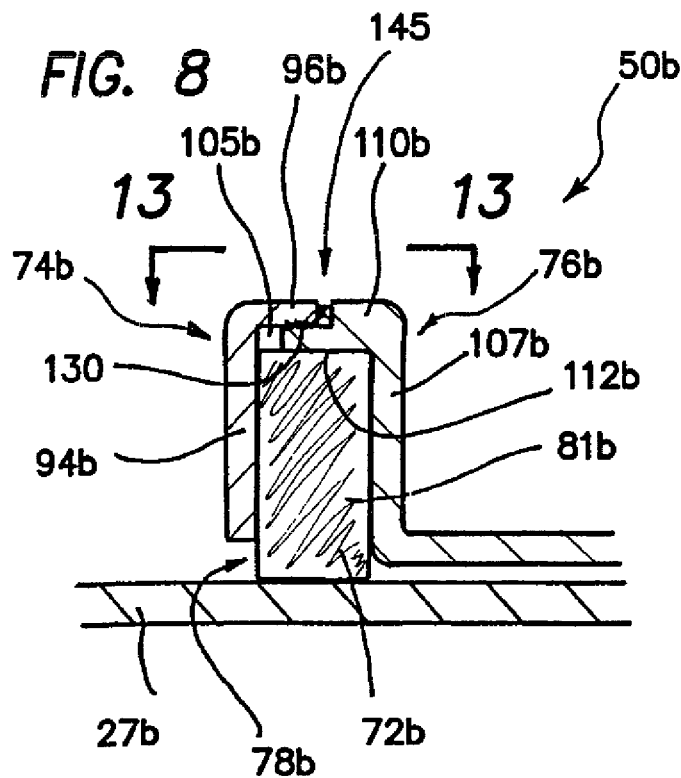
FIG. 8 is an axial cross-section view of an embodiment which provides control of the expansion cavity to produce a locking force on the instrument.

In a further embodiment illustrated in FIG. 8, elements of structure similar to those previously discussed are designated with the same reference numeral followed by the lower case letter "b" Thus, the embodiment of FIG. 8 includes the proximal housing portion 74b, with the radial wall 94b and associated cylindrical wall 96b. This embodiment also includes the distal housing portion 76b with a generally radial wall 107b and shoulder 110b integral with the axial wall 112b. The plug 81b of gel 72b is disposed in the gel cavity 78b.

Figure 9:
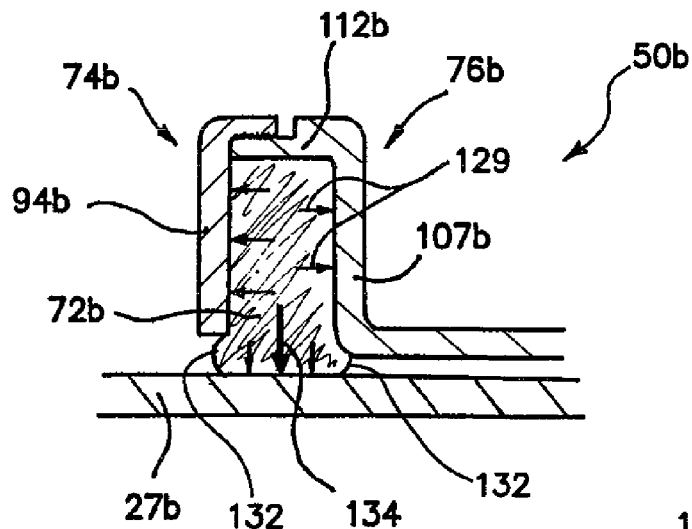
FIG. 9 is an axial cross-section view illustrating substantial elimination of the expansion cavity to increase the area and pressure of the instrument seal.

The guidewire 27b is also illustrated in FIG. 8 after it has been loaded into the valve 50b in the manner previously discussed. During this loading step, the guidewire 27b takes advantage of the low friction forces but the high sealing characteristics provided by the gel 72b. While these advantages can be particularly appreciated when the guidewire 27b is loaded into the valve 50b, it may be desirable after the loading step, to increase the resistance between the gel 72b and the guidewire 27b or otherwise lock the guidewire 27b in place. In the embodiment of FIG. 8, this locking feature is facilitated by screw threads 130 which are disposed on the cylindrical wall 96b of the proximal housing portion 74b, and the axial wall 112b of the distal housing portion 76b. As the proximal housing portion 74b is rotated on its axis relative to the distal housing portion 76b, the radial wall 94b approaches the radial wall 107b This has two effects. Initially, it tends to eliminate or at least reduce the size of the expansion cavity portion 105b. It also creates a force on the plug 81b. Since the plug 81b is formed of the gel 72b with non-compressible characteristics, any force applied to is the gel 72b results in a pressure within the plug 81b. This pressure is represented in FIG. 9 by arrows 129. With the gel cavity 78b defined by rigid walls 94b, 107b and 112b, the pressure within the gel 72b forces the gel 72b to move into any open space. With the elimination of the expansion cavity portion 105b, as illustrated in FIG. 9, the gel tends to expand into any openings which may exist between the guidewire 27b and the valve 50b. In FIG. 9, this movement is shown by a pair of bulges 132 which notably increase the area of contact between the gel 72b and the guidewire 27b. With an increase in the pressure within the gel 72b, a force shown by arrow 134 is directed against the guidewire 27b tending to lock it in place relative to the valve 50b.

The screw threads 130 are of particular advantage in producing the locking force shown by arrow 134, because they can provide a significant mechanical advantage. However, it will be appreciated by those skilled in the art that there are many other mechanisms which can be used to compress the cavity 78b between the walls 94b and 107b.

Figure 10:
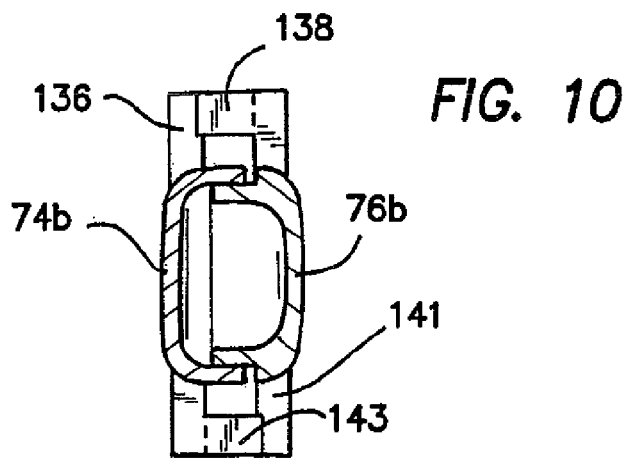
FIG. 10 is an axial cross-section illustrating two tab pairs operable to alternatively increase and decrease the instrument locking pressure.

As illustrated in FIG. 10, the threads 130 (FIG. 8) offer a further advantage in facilitating one-handed control of the size of the cavity 78b. As illustrated in the side view of FIG. 10, a pair of tabs 136 and 138 can be attached to the housing portions 74b and 76b, respectively, in an upper region of the valve 50b. Similarly, a pair of tabs 141 and 143 can be attached to the housing portions 74b and 76b, respectively, in a lower region of the valve 50b. These tab pairs are further illustrated in the front elevation view of FIG. 11 where the tabs 136 and 141 can be separated by an angular distance such as 150 degrees on the proximal housing portion 74b. Similarly, the tabs 138 and 143 can be separated by an angle such as 150 degrees.

Figure 11:
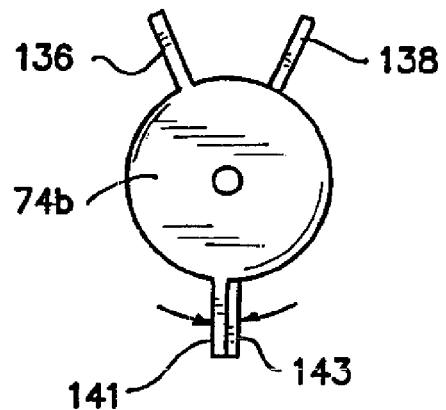
FIG. 11 is a front plan view illustrating compression of one of the tab pairs to reduce the locking pressure.
Figure 12:
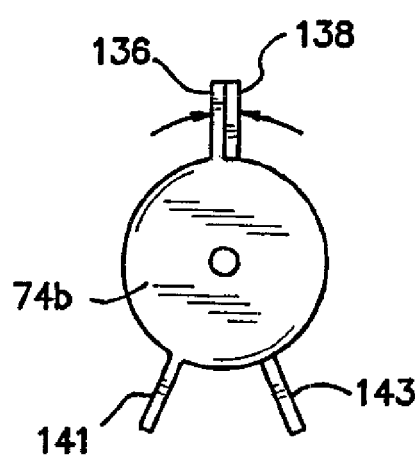
FIG. 12 is a top plan view illustrating compression of the other tab pair to increase the locking pressure.

When the upper tab pair including the tabs 136 and 138 are pinched into juxtaposition as illustrated in FIG. 12, the proximal housing portion 74b moves axially toward the distal housing portion 76b at a rate dependent on the pitch of the threads 130. As this movement occurs by the simple pinching action on the two tabs 136 and 138, the size of the gel cavity 72b is decreased and the locking force represented by the arrow 134 is applied to the guidewire 27b. When it is desired to remove the guidewire 27b, this locking force can be removed by merely pinching the lower tab pair including the tabs 141 and 143. This will place the tabs 141 and 143 in juxtaposition as illustrated in FIG. 11. The proximal housing portion 74b rotates counterclockwise relative to the distal housing portion 76b thereby increasing the size of the gel cavity 78b and appropriately decreasing the locking force represented by arrow 134.

Figure 13:
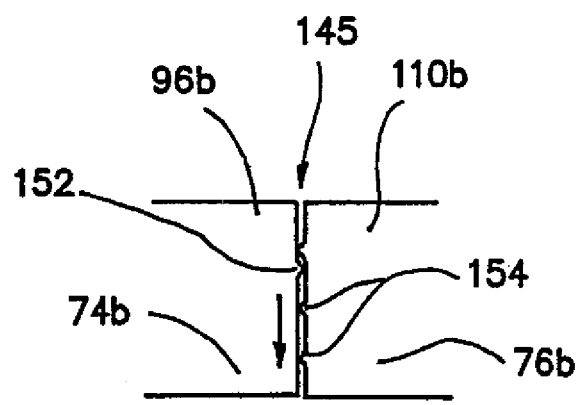
FIG. 13 is a top plan view taking along lines 13-13 of FIG. 8 and illustrating one embodiment of a detent mechanism.

With a structure similar to that in FIGS. 8-12, the magnitude of the locking force represented by the arrow 134 is dependent upon the degree of separation between the tabs 136 and 138. The maximum locking force is provided when the tabs 136 and 138 are positioned as illustrated in FIG. 12. The minimum force is applied when the tabs 136 and 138 are maximally separated as illustrated in FIG. 11. Between these two extremes, a detent mechanism 145 can be provided so that the desired degree of locking force 134 can be achieved by movement of the tabs 136 and 138. This mechanism can include interfering projections 152 and 154 formed on the cylindrical walls 96b and shoulder 110b, respectively, as illustrated in FIG. 13. As the tabs 136 and 138 are closed to move the proximal housing portion 74b axially toward the distal housing portion 76b, these interfering projections 152 and 154 will detent to define a variable locking force represented by the arrow 134. The detent projections 152 and 154 in this case are disposed axially relative to each other.

Figure 14:
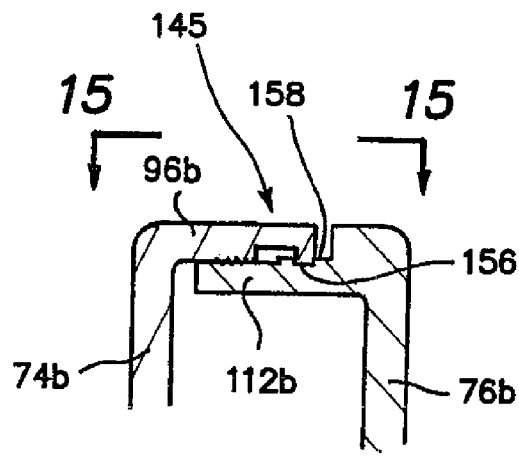
FIG. 14 is an axial cross section view illustrating another embodiment of a detent mechanism.
Figure 15:
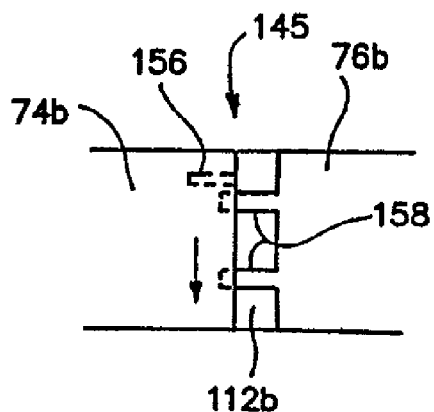
FIG. 15 is a top plan view taken along lines 15-15 of FIG. 14.

In a further embodiment illustrated in FIG. 14, a detent mechanism 145 is formed between projections 156 and 158 that are oriented in a radial direction. The projection 156 is disposed to extend radially on the underside of the cylindrical wall 96b while the projections 158 extend upwardly from the axial wall 112b. As in the previous embodiment, the detent mechanism 145 of FIGS. 14 and 15 will function to define a variable locking force represented by the arrow 134.

A preferred method for manufacturing the valve 50 contemplates use of a mandrel. Initially it will be noted that the various parts of the valve 50, including the proximal housing portion 74, the distal housing portion 76, the plug 81, and the screw cap 87, each have an axial hole or channel in the assembly of the valve. This enables the various parts to be threaded onto the mandrel which can be used to guide the various structural elements axially to their assembled relationship.

In a preferred method of manufacture, the distal housing portion 76a is initially placed on the mandrel. Then the plug 81a can be threaded onto the mandrel through the channel 101a. The mandrel holds these two elements in exact axial alignment so that the plug 81a can merely be pushed along the mandrel and into the gel cavity 78a. At this point, the lead-in tube 125 of the proximal housing portion 74a can be threaded onto the mandrel. Again, the mandrel holds this part in axial alignment with the prior subassembly. With this alignment ensured, the proximal housing portion 74a can merely be pushed generally onto the distal housing portion 76a to compress the plug 81a. The wall 96a of the proximal housing portion 74a and the wall 112 of the distal housing portion 76a can then be joined by a snap fit, glue or preferably a sonic weld. Finally, the Luer cap 87a can be threaded onto the mandrel and moved into a snap fit, rotatable relationship with the Luer fitting 85.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

The invention claimed is:

1. A surgical valve having an axis extending between a proximal end and a distal end, comprising:
   a housing including a proximal housing portion and a distal housing portion adjustably cooperating with the proximal housing portion to define a gel cavity;
   a seal material disposed in the gel cavity, the seal material including a gel having non-compressible characteristics, the gel having characteristics for creating a pressure on an instrument extending through the valve to form a seal around the instrument;
   a proximal guide tube extending axially proximally from the proximal housing portion;
   the proximal guide tube facilitating insertion of a surgical instrument into the seal material; and
   a distal guide tube extending axially distally from the distal housing portion, the distal guide tube facilitating retrograde insertion of the surgical instrument into the surgical seal, wherein the proximal guide tube includes exterior portions extending proximally of the proximal housing portion and interior portions extending distally of the proximal housing portion, wherein
   the proximal housing portion is adjustably movable axially relative to the distal housing portion to increase the pressure of the incompressible gel on the instrument and to create a locking force tending to inhibit movement of the instrument relative to the valve.

2. The surgical valve recited in claim 1, further comprising:
   a Luer lock coupled to the distal housing portion; and
   the distal guide tube being included within the Luer lock.

3. The surgical valve recited in claim 1, wherein:
   the seal material defines an axial channel through the gel; and
   the proximal guide tube contacts the seal material around the axial channel at the proximal end of the valve.

4. The surgical valve recited in claim 1, wherein:
   the seal material and the distal housing portion form a subassembly free of a circumferential seal between the seal material and the distal housing portion; and
   the proximal guide tube applies a force to the seal material in the subassembly to form a circumferential seal between the gel and the distal housing portion.

5. A surgical valve, comprising:
   a first housing portion defining a gel cavity;
   a seal material including a gel and having a node and an axial channel;
   a subassembly including the seal material disposed in the gel cavity, the seal material being configured with the channel in an open state; and
   a second housing portion disposed in juxtaposition to the first housing portion and applying a force to the seal material in the subassembly, the force being of a magnitude sufficient to place the channel of the seal material in a closed state.

6. The surgical valve recited in claim 5, wherein the second housing portion applies the force to the seal material with a magnitude sufficient to create a circumferential seal between the seal material and the first housing portion.

7. The surgical valve recited in claim 6, wherein the second housing portion includes an axial guide tube, and the guide tube applies the force to the seal material in the subassembly.

8. The surgical valve recited in claim 7 wherein the guide tube contacts the node of the seal material to apply the force to the seal material.

9. A surgical valve adapted to form a seal around a surgical instrument extending through the valve, comprising:
   a first housing portion;
   a second housing portion adjustably engaging the first housing portion and defining with the first housing portion a gel cavity having a volume;
   a gel disposed within the gel cavity and having properties including flowability and incompressibility, the gel having characteristics for creating a pressure on the instrument to form a seal with the instrument, wherein
   the second housing portion is adjustably movable axially relative to the first housing portion to increase the pressure of the incompressible gel on the instrument and to create a locking force tending to inhibit movement of the instrument relative to the valve.

10. The surgical valve recited in claim 9 wherein the first housing portion and the second housing portion comprise:
    complimentary screw threads disposed on the first housing portion and the second housing portion, the screw threads facilitating axial movement of the first housing portion relative to the second housing portion to reduce the volume of the gel cavity and to create the locking force between the incompressible gel and the instrument.

11. The surgical valve recited in claim 10, further comprising:
    a first tab fixed to the first housing portion;
    a second tab fixed to the second housing portion;
    the first tab and the second tab forming a first tab pair moveable relative to each other to decrease the volume of the gel cavity.

12. The surgical valve recited in claim 11, further comprising:
    a third tab fixed to the first housing portion;
    a fourth tab fixed to the second housing portion;
    the third tab and the fourth tab forming a second tab pair moveable relative to each other to increase the volume of the gel cavity.

13. The surgical valve recited in claim 12, wherein the first valve pair is disposed on a side of the valve opposing the second tab pair.

14. The surgical valve recited in claim 12 wherein the fourth tab of the second tab pair is integral with the second tab of the first tab pair.

* * * * *